US006861051B2

(12) United States Patent
Moore

(10) Patent No.: US 6,861,051 B2
(45) Date of Patent: Mar. 1, 2005

(54) 1,2-PROPYLENE GLYCOL SKIN PREPARATION SOLUTION AND METHOD OF USE THEREOF

(75) Inventor: Milton D. Moore, 9350 Kirby Dr., Ste. 100A, Houston, TX (US) 77054-2515

(73) Assignee: Milton D. Moore, Houston, TX (US)

(*) Notice: Subject to any disclaimer, the term of this patent is extended or adjusted under 35 U.S.C. 154(b) by 284 days.

(21) Appl. No.: 10/208,479

(22) Filed: Jul. 30, 2002

(65) Prior Publication Data

US 2004/0022756 A1 Feb. 5, 2004

(51) Int. Cl.[7] ................................................. A61K 7/15
(52) U.S. Cl. ..................... 424/73; 424/401; 424/409; 424/73; 514/844; 514/846
(58) Field of Search .......................... 424/401, 409, 424/73; 514/844, 846

(56) References Cited

U.S. PATENT DOCUMENTS

| | | | |
|---|---|---|---|
| 3,472,940 A | 10/1969 | Osipow et al. ............ 424/365 |
| 3,715,942 A | 2/1973 | Courtney et al. ............. 83/22 |
| 4,737,360 A | * 4/1988 | Allen et al. ................ 424/60 |
| 4,831,023 A | 5/1989 | Garlen et al. ............... 514/169 |
| 4,944,939 A | 7/1990 | Moore ........................ 424/73 |
| 5,387,412 A | 2/1995 | Moore ........................ 424/73 |
| 6,415,800 B2 | * 7/2002 | Poisson et al. ............. 132/200 |

OTHER PUBLICATIONS

CUTIS vol. 68, Dec. 2001; Therapeutic Moisturizers (pp. 4–20).

* cited by examiner

Primary Examiner—Thurman K. Page
Assistant Examiner—Micah-Paul Young
(74) Attorney, Agent, or Firm—Conley Rose, P.C.

(57) ABSTRACT

A skin preparation solution for application to the surface of the skin prior to shaving or application of topical medications or other topically applied substances, to improve penetration and sustain levels of the treatments within the skin. The solution of the present invention contains (all percentages by volume) between ten and eighty percent, and preferably about 44.5 percent, of 1,2-propylene glycol, between ten and eighty percent, and preferably about 55 percent, of deionized water, between 0.02 and four percent, and preferably 0.2 percent, of imidazolidinyl urea, between 0.02 and four percent, and preferably 0.2 percent, of methylparaben, between 0.01 and two percent, and preferably 0.1 percent, of propylparaben, and optionally, between 0.2 and ten percent, and preferably one percent, of aloe vera, and between 0.2 and ten percent, and preferably one percent, of polysorbate-20.

24 Claims, No Drawings

1,2-PROPYLENE GLYCOL SKIN PREPARATION SOLUTION AND METHOD OF USE THEREOF

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The invention relates generally to a skin preparation solution. In particular, the invention relates to an aqueous 1,2-propylene glycol solution, optionally containing aloe, suitable for pre-treating skin prior to shaving or the application of topical medications, transdermal patches, sunscreens or other topically applied treatments.

BACKGROUND OF THE INVENTION

Topical medications, or drugs applied to the surface of the skin, are available in gel, foam, ointment, cream and other bases. Topical medications generally operate by passing through the surface of the skin, through the uppermost layer of skin, or epidermis, and into the underlying skin layer, the dermis. Some topical medications may penetrate even deeper, into the tissue fluid underlying the dermis, producing a therapeutic effect in a greater distributed area around the spot of application, or even producing a more systemic, or body-wide, effect.

In addition to the potency of a topical drug, other factors also contribute to the effectiveness of a drug. Increasing the rate of penetration, characterized as the amount of drug penetrating into the skin per unit of time, also lessens the time it takes for an effective amount of the drug to become present in the skin. Sustaining the rate of penetration after initial application ensures that the drug is still actively passing through the skin long after it is applied, contributing to the length of time a drug may be effective before needing reapplication. Consequently, improving the initial penetration rate and sustaining a high rate of penetration long after application can yield a higher cumulative amount of drug penetration.

Moreover, the depth of penetration is also important, since a more widespread or systemic effect can often be achieved the deeper a drug penetrates into the skin. Further, the distribution of the drug into the skin, or amount of drug retained in a particular skin layer (as a percentage of applied dose), is an indicator of how much drug is present in the layer in which it is most therapeutic.

As topical drugs can be expensive, it would be of particular benefit to increase the effectiveness of topically applied medications. Generally, once a drug is applied to the skin, the amount of drug passing through the skin increases from zero to a peak rate relatively quickly, then tends to drop off as time elapses. Increasing initial penetration rate and sustaining a steady penetration rate for a longer time after application would be beneficial.

Luxíq® is the brand name of a foam-based topical corticosteroid formulation of the prescription drug betamethasone valerate. After applying a dose of Luxíq to skin pre-treated with a 1,2-propylene glycol and mineral oil solution, initial penetration rates of the drug through the surface of the skin are significantly lower compared to a control application of the drug with no skin pre-treatment. However, the sustained penetration rate of the skin pre-treated with the prior art solution shows improvement over that of untreated skin, with a smaller decrease in penetration rate over several hours.

With the pre-treated skin, the cumulative amount of the drug penetrating through the skin over time shows slight improvement over that of the control drug application. Distribution of the drug in the epidermis, as a percentage of applied dosage, also shows slight improvement. However, distribution of the drug in the dermis and tissue fluid shows a marked decrease and little change, respectively. As Luxíq is most therapeutic in the dermis, and pre-treatment of the skin with the prior art solution has been shown to hinder, and therefore not significantly improve, penetration to this layer, a more effective skin pre-treatment composition is desired.

Transdermal patches are medicated patches applied to the skin having treatments intended to pass through the skin to have a therapeutic or preventive effect, including patches for motion sickness, heart medication, contraception, asthma, and smoking cessation. Many transdermal patches would benefit from more rapid and longer sustained effectiveness. In the case of heart patients or asthma patients, it may be critical for the therapeutic effect of the patch to be more immediate. Maintaining more constant drug levels in the skin would be greatly beneficial to many applications, including motion sickness, contraception and smoking cessation treatments.

Sunscreens also would benefit from quicker penetration, a higher rate of penetration and longer sustained penetration. Most sunscreens require application up to a half an hour before sun exposure to become effective, and also require frequent application in order to maintain protection. A solution is desired in order to make sunscreens effectively more quickly and for a longer duration, to prevent early burning and sun damage that may occur before the sunscreen becomes effective.

Topical skin preparation can also be beneficial prior to shaving. For conventional shaving with a safety razor or a straight razor, once the area to be shaved is wetted, a shaving soap or foam is applied in order to more fully hydrate the hairs. This procedure is followed both by males, when shaving the beard, and by women, when shaving legs, underarms, facial hair, or the bikini line. One disadvantage associated with shaving soaps and foams is that the hydration of the hairs is not complete, and thus they often do not lubricate well at the razor edge. The razor can tend to stick, leading to nicks, cuts, or skin irritation. In addition, the soaps or foams tend to desiccate the skin, and creams or emollients must often be applied after shaving to re-hydrate the skin.

Accordingly, in addition to the topical treatments discussed above, a shaving solution is desired that would provide a more effective and pleasant shaving method without requiring additional moisturizing subsequent to shaving.

SUMMARY OF THE INVENTION

The skin preparation solution of the present invention includes an aqueous skin preparation solution preferably containing about ten percent to about eighty percent, and preferably about 44.5 percent, by volume of 1,2-propylene glycol; about ten to eighty percent, and preferably 55 percent, by volume of deionized water; about 0.02 percent to about four percent, and preferably 0.2 percent, by volume of imidazolidinyl urea; about 0.02 percent to about four percent, and preferably 0.2 percent, by volume of methylparaben; about 0.01 percent to about two percent, and preferably 0.1 percent, by volume of propylparaben; and optionally, about 0.2 percent to about ten percent, and preferably one percent, by volume of aloe vera, preferably in the form of a powder extract; and about 0.2 percent to about ten percent, and preferably one percent, by volume of polysorbate-20 as a wetting agent for the aloe vera. If aloe and polysorbate-20 are included in the solution, water and propylene glycol are preferably reduced equally to account for the added volumes of aloe and polysorbate-20.

The solution of the present invention can applied to the surface of the skin prior to the application of a topical treatment, such as a medication or sunscreen, to improve penetration and retention of the treatment in the skin. After pre-treatment of the skin with the solution, topical drugs and other skin treatments generally will show an increased initial penetration rate, a longer sustained peak penetration, and greater retention in the layers of the skin, therefore improving and sustaining the effectiveness of topically applied skin treatments.

The solution of the present invention can be also used as a substitute for conventional shaving preparations, including shaving soaps or foams and water, and other shaving preparations, in order to more fully hydrate the hairs to be shaved and provide lubrication and moisturizing of the skin. In use, the area to be shaved is flooded with the solution of the present invention. The solution of the present invention is preferably applied to the skin, which is then subsequently shaved with a conventional safety or straight-edge razor.

Thus, the present invention comprises a combination of features and advantages that enable it to overcome various problems of prior compositions. The various characteristics described above, as sell as other features, will be readily apparent to those skilled in the art upon reading the following detailed description of the preferred embodiments of the invention.

DETAILED DESCRIPTION OF THE PREFERRED EMBODIMENT

In the preferred embodiment of the present invention, the skin preparation solution of the present invention is an aqueous solution preferably containing about ten percent to about eighty percent by volume of 1,2-propylene glycol, about ten to eighty percent by volume of deionized (DI) water, about 0.02 percent to about four percent by volume of imidazolidinyl urea, about 0.02 percent to about four percent by volume of methylparaben, and about 0.01 percent to about two percent by volume of propylparaben.

More preferably, the preferred skin preparation solution of the present invention contains about twenty percent to about seventy percent by volume of 1,2-propylene glycol, about twenty to seventy percent by volume of DI water, about 0.05 percent to about three percent by volume of imidazolidinyl urea, about 0.05 percent to about three percent by volume of methylparaben, and about 0.03 percent to about three percent by volume of propylparaben.

Still more preferably, the preferred skin preparation solution of the present invention contains about thirty percent to about sixty percent by volume of 1,2-propylene glycol, about thirty to sixty percent by volume of DI water, about 0.1 percent to about two percent by volume of imidazolidinyl urea, about 0.1 percent to about two percent by volume of methylparaben, and about 0.05 percent to about one percent by volume of propylparaben.

Most preferably, the preferred skin preparation solution of the present invention contains about 44.5 percent by volume of 1,2-propylene glycol, about 55 percent by volume of DI water, about 0.2 percent by volume of imidazolidinyl urea, about 0.2 percent by volume of methylparaben, and about 0.1 percent by volume of propylparaben.

In an alternate embodiment of the present invention, aloe vera, preferably in the form of a powder extract, is added to the solution, along with polysorbate-20 as a wetting agent for the aloe. An alternate skin preparation solution of the present invention preferably contains about ten percent to about eighty percent by volume of 1,2-propylene glycol, about ten to eighty percent by volume of DI water, about 0.02 percent to about four percent by volume of imidazolidinyl urea, about 0.02 percent to about four percent by volume of methylparaben, about 0.01 percent to about two percent by volume of propylparaben, about 0.2 percent to about ten percent by volume of aloe vera, and about 0.2 percent to about ten percent by volume of polysorbate-20.

More preferably, an alternate skin preparation solution of the present invention contains about twenty percent to about seventy percent by volume of 1,2-propylene glycol, about twenty to seventy percent by volume of DI water, about 0.05 percent to about three percent by volume of imidazolidinyl urea, about 0.05 percent to about three percent by volume of methylparaben, about 0.03 percent to about three percent by volume of propylparaben, about one-half percent to about five percent by volume of aloe vera, and about one-half percent to about five percent by volume of polysorbate-20.

Still more preferably, an alternate skin preparation solution of the present invention contains about thirty percent to about sixty percent by volume of 1,2-propylene glycol, about thirty to sixty percent by volume of DI water, about 0.1 percent to about two percent by volume of imidazolidinyl urea, about 0.1 percent to about two percent by volume of methylparaben, about 0.05 percent to about one percent by volume of propylparaben, about 0.8 percent to about three percent by volume of aloe vera, and about 0.8 percent to about three percent by volume of polysorbate-20.

Most preferably, an alternate skin preparation solution of the present invention contains about 43.5 percent by volume of 1,2-propylene glycol, about 54 percent by volume of DI water, about 0.2 percent by volume of imidazolidinyl urea, about 0.2 percent by volume of methylparaben, about 0.1 percent by volume of propylparaben, about one percent by volume of aloe vera, and about one percent by volume of polysorbate-20.

As drugs are available in different bases of varying consistencies, such as foams or ointments, the percentages of propylene glycol and aloe (if included) can be varied according to the consistency of the base and/or drug that is to be used so as to achieve optimal results. The solution may also contain additives, for example, scents, perfumes, or alternate preservatives, if so desired, and is applied to the surface of the skin prior to shaving or application of a topical treatment such as a topical medication or sunscreen.

When a skin preparation solution according to the preferred embodiment of the present invention is applied to the skin, followed by application of the drug Luxíq, the initial penetration rate of the drug shows an increase when compared to the penetration rate of a control application of Lux íq with no skin pre-treatment. Additionally, the rate of penetration does not decrease as rapidly as that of the control, but is more steadily sustained, showing twice the penetration rate of the control after a 24-hour period. Accordingly, the cumulative drug penetration over a 24-hour period after pre-treatment also shows a marked increase, with approximately twice the amount of drug penetrated into the skin as compared to a control application with no pre-treatment.

As Luxíq and many other topical drugs are most therapeutic in the dermis layer, it is desirable to ensure that a greater percentage of the total applied dose reaches and is retained in this layer. When measured as a percentage of applied dose, drug distribution in the dermis, when pre-treated with the solution of the present invention, shows the most distinct improvement, nearly doubling the amount of drug retained in the dermis when compared to skin that was not pre-treated. Drug retention in the epidermis shows a marginal increase and retention in the tissue fluid is also nearly doubled from the untreated skin. Comparable results are anticipated for other topical drugs and treatments, as the operating methods of skin penetration are generally similar.

Skin includes both an oil component and a water component. Common commercially available moisturizers often also contain both oil and water components, in order to loosely mimic skin's own natural lubrication and to assist in augmenting lubrication already found in the skin, which exists naturally to prevent excessive moisture loss from the skin to the environment. A solution with components having both oil and water in a suspension arrangement similar to that required for passage through the skin allows a drug to break through these barriers and pass into the skin, where it can be therapeutic. In the solution of the present invention, propylene glycol serves as an agent to keep oil found in the aloe in a suitable suspension with the water.

Aloe vera may optionally be added to the solution of the present invention, as it is known to have an oil component in addition to a water component, making it suitable for preparing the skin for drug penetration. Aloe is also not as thick in consistency as the mineral oil base used in certain prior art pre-treatment solutions. Whereas aloe is a combination of water and oil components and can provide a skin preparation with the desired mixture of oil and water properties, mineral oil may actually block initial penetration of the drug into the skin, owing to its relatively thick, oily consistency and lack of a water component.

As pre-treating the skin with the solution of the present invention is almost instantly effective, there is no need to wait to apply the drug before penetration improvements can be achieved. This may be a significant advantage in sunscreen effectiveness, helping the sunscreen become effective more quickly after application, and preventing a degree of early burning or photoaging of the skin, which may occur after sunscreen application but before the sunscreen has taken effect. Additionally, maintaining peak levels of sunscreen in the skin may aid in sustaining sunscreen effectiveness, so skin will be protected longer between applications.

The propylene glycol solution of the present invention can also be used to avoid shaving discomfort and wounds to human skin. If the concentration of 1,2-propylene glycol is substantially less than about fifty percent by volume, hydration and lubrication are less than is desired, resulting in increased and unacceptable incidence of nicks and cuts. If the 1,2-propylene glycol concentration is greater that about eighty percent by volume, the solution tends to become oily and less effective as a hydrating agent because the water concentration becomes too low. Increasing the optional aloe vera concentration in the solution would tend to make the solution slicker.

To use the solution of the present invention, the solution of the present invention is liberally applied to the human skin area to be shaved, "flooding" the skin area with the solution. Preferably, the solution is applied in atomized form, such as with a pump spray or similar apparatus. However, the solution can be applied by other means, such as by splashing or pouring on the areas to be shaved. The skin is then shaved with a razor, and after shaving, the excess solution and cut hairs are wiped off the skin. There is no need to rinse the shaved area because the solution of the present invention moisturizes the skin and leaves it soft and moist. The solution of the present invention can also be used as a moisturizer in areas of the body that do not require shaving.

Because of its lubricating qualities, the skin preparation solution of the present invention is well suited for those who suffer from mild forms of razor bumps, otherwise known as pseudofolliculitis barbae ("PFB"). For more severe PFB cases, the system disclosed in U.S. Pat. No. 4,944,939 should be used. The present skin preparation solution is also recommended for use by those with milder forms of shaving irritation, such as razor rash, and for persons with sensitive skin.

It should be understood that the foregoing terms, expressions, and examples are exemplary only and not limiting, and that the scope of protection is defined only by the claims that follow and includes all equivalents of the subject matter of those claims.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A topical composition consisting of:

from ten percent to about eighty percent by volume of 1,2-propylene glycol;

from about ten percent to eighty percent by volume of deionized water;

from about 0.02 percent to about four percent by volume of imidazolidinyl urea;

from about 0.02 percent to about four percent by volume of methylparaben; and from about 0.01 percent to about two percent by volume of propylparaben.

2. A topical composition consisting of:

from about ten percent to about eighty percent by volume of 1,2-propylene glycol;

from about ten percent to eighty percent by volume of deionized water;

from about 0.02 percent to about four percent by volume of imidazolidinyl urea;

from about 0.02 percent to about four percent by volume of methylparaben;

from about 0.01 percent to about two percent by volume of propylparaben;

from about 0.2 percent to about ten percent by volume of aloe vera; and from about 0.2 percent to about ten percent by volume of polysorbate-20.

3. A method of preparing skin for application of a topical treatment, comprising the steps of:

applying to the skin an aqueous solution consisting of from about ten percent to about eighty percent by volume of 1,2-propylene glycol, from about ten percent to eighty percent by volume of deionized water, from about 0.02 percent to about four percent by volume of imidazolidinyl urea, from about 0.02 percent to about four percent by volume of methylparaben, and from about 0.01 percent to about two percent by volume of propylparaben; and applying the topical treatment.

4. The method of claim 3 wherein the solution is applied in atomized form.

5. The method of claim 4 wherein the solution is applied with a pump spray apparatus.

6. A method of preparing skin for application of a topical treatment, comprising the steps of:

applying to the skin an aqueous solution consisting of from about ten percent to about eighty percent by volume of 1,2-propylene glycol, from about ten to eighty percent by volume of deionized water, from about 0.02 percent to about four percent by volume of imidazolidinyl urea, from about 0.02 percent to about four percent by volume of methylparaben, from about 0.01 percent to about two percent by volume of propylparaben, from about 0.2 percent to about ten percent by volume of aloe vera, and from about 0.2 percent to about ten percent by volume of polysorbate-20; and applying the topical treatment.

7. The method of claim 6 wherein the solution is applied in atomized form.

8. The method of claim 7 wherein the solution is applied with a pump spray apparatus.

9. A method of preparing skin for application of a topical treatment, comprising the steps of:

applying to the skin an aqueous solution consisting of about 44.5 percent by volume of 1,2-propylene glycol, about 55 percent by volume of DI water, about 0.2 percent by volume of imidazolidinyl urea, about 0.2 percent by volume of methylparaben, and about 0.1 percent by volume of propylparaben; and applying the topical treatment.

10. A method of preparing skin for application of a topical treatment, comprising the steps of:

applying to the skin an aqueous solution consisting of about 43.5 percent by volume of 1,2-propylene glycol, about 54 percent by volume of deionized water, about 0.2 percent by volume of imidazolidinyl urea, about 0.2 percent by volume of methylparaben, about 0.1 percent by volume of propylparaben, about one percent by volume of aloe vera, and about one percent by volume of polysorbate-20; and applying the topical treatment.

11. A method of preparing a human skin area for shaving, comprising the steps of:

flooding the human skin area to be shaved with an aqueous solution consisting of from about ten percent to about eighty percent by volume of 1,2-propylene glycol, from about ten percent to eighty percent by volume of deionized water, from about 0.02 percent to about four percent by volume of imidazolidinyl urea, from about 0.02 percent to about four percent by volume of methylparaben, and from about 0.01 percent to about two percent by volume of propylparaben.

12. The method of claim 11, further comprising the steps of:

applying a hot, wet towel to the human skin area to be shaved; and flooding the human skin area to be shaved with an aqueous solution consisting of from about ten percent to about eighty percent by volume of 1,2-propylene glycol, from about ten percent to eighty percent by volume of deionized water, from about 0.02 percent to about four percent by volume of imidazolidinyl urea, from about 0.02 percent to about four percent by volume of methylparaben, and from about 0.01 percent to about two percent by volume of propylparaben; and shaving the flooded skin area.

13. The method of claim 12 further including the step of wiping excess shaving solution and hairs from the shaved area.

14. The method of claim 11 wherein the solution is applied in atomized form.

15. The method of claim 14 wherein the solution is applied with a pump spray apparatus.

16. A method of preparing a human skin area for shaving, comprising the steps of:

flooding the human skin area to be shaved with an aqueous solution consisting of from about ten percent to about eighty percent by volume of 1,2-propylene glycol, from about ten percent to eighty percent by volume of deionized water, from about 0.02 percent to about four percent by volume of imidazolidinyl urea, from about 0.02 percent to about four percent by volume of methylparaben, from about 0.01 percent to about two percent by volume of propylparaben, from about 0.2 percent to about ten percent by volume of aloe vera, and from about 0.2 percent to about ten percent by volume of polysorbate-20.

17. The method of claim 16, further comprising the steps of:

flooding the human skin area to be shaved with an aqueous solution consisting of from about ten percent to about eighty percent by volume of 1,2-propylene glycol, from about ten percent to eighty percent by volume of deionized water, from about 0.02 percent to about four percent by volume of imidazolidinyl urea, from about 0.02 percent to about four percent by volume of methylparaben, from about 0.01 percent to about two percent by volume of propylparaben, from about 0.2 percent to about ten percent by volume of aloe vera, and from about 0.2 percent to about ten percent by volume of polysorbate-20; and shaving the flooded skin area.

18. The method of claim 17 further including the step of wiping excess shaving solution and hairs from the shaved area.

19. The method of claim 16 wherein the solution is applied in atomized form.

20. The method of claim 19 wherein the solution is applied with a pump spray apparatus.

21. A method of preparing a human skin area for shaving, comprising the steps of:

flooding the human skin area to be shaved with an aqueous solution consisting of about 44.5 percent by volume of 1,2-propylene glycol, about 55 percent by volume of deionized water, about 0.2 percent by volume of imidazolidinyl urea, about 0.2 percent by volume of methylparaben, and about 0.1 percent by volume of propylparaben.

22. The method of claim 21, further comprising the steps of:

flooding the human skin area to be shaved with an aqueous solution consisting of about 44.5 percent by volume of 1,2-propylene glycol, about 55 percent by volume of deionized water, about 0.2 percent by volume of imidazolidinyl urea, about 0.2 percent by volume of methylparaben, and about 0.1 percent by volume of propylparaben; and shaving the flooded skin area.

23. A method of preparing a human skin area for shaving, comprising the steps of:

flooding the human skin area to be shaved with an aqueous solution consisting of about 43.5 percent by volume of 1,2-propylene glycol, about 54 percent by volume of deionized water, about 0.2 percent by volume of imidazolidinyl urea, about 0.2 percent by volume of methylparaben, about 0.1 percent by volume of propylparaben, about one percent by volume of aloe vera, and about one percent by volume of polysorbate-20.

24. The method of claim 23, further comprising the steps of:

flooding the human skin area to be shaved with an aqueous solution consisting of about 43.5 percent by volume of 1,2-propylene glycol, about 54 percent by volume of deionized water, about 0.2 percent by volume of imidazolidinyl urea, about 0.2 percent by volume of methylparaben, about 0.1 percent by volume of propylparaben, about one percent by volume of aloe vera, and about one percent by volume of polysorbate-20; and shaving the flooded skin area.

* * * * *